(12) United States Patent
Kirschbaum

(10) Patent No.: US 6,186,940 B1
(45) Date of Patent: Feb. 13, 2001

(54) ENERGIZED TRACE ELEMENTS

(76) Inventor: Robert N. Kirschbaum, 6630 E. Exposition Ave., Denver, CO (US) 80224-1507

( * ) Notice: Under 35 U.S.C. 154(b), the term of this patent shall be extended for 0 days.

(21) Appl. No.: 09/313,472

(22) Filed: May 17, 1999

Related U.S. Application Data

(60) Provisional application No. 60/085,917, filed on May 18, 1998, now abandoned.

(51) Int. Cl.[7] .............................. A61M 37/00; A61N 2/00
(52) U.S. Cl. ................................................................ 600/12
(58) Field of Search ......................................... 600/12, 13

(56) References Cited

U.S. PATENT DOCUMENTS

| | | | |
|---|---|---|---|
| 5,162,037 | * | 11/1992 | Whitson-Fischman ................ 600/12 |
| 5,269,746 | * | 12/1993 | Jacobson ................................ 600/13 |

* cited by examiner

*Primary Examiner*—Max Hindenburg
*Assistant Examiner*—Brian Szmal
(74) *Attorney, Agent, or Firm*—Ramon L. Pizarro; Edwin H. Crabtree

(57) ABSTRACT

A way to supplement the electrical component of all living organisms has been discovered, and is disclosed herein. This is accomplished by passing electrical currents through elements and/or compounds in an aqueous environment. The elements and/or compounds gather electrical energy from the electrical current. The energized or magnetized elements are then given to the living organisms.

20 Claims, No Drawings

ENERGIZED TRACE ELEMENTS

REFERENCE TO RELATED APPLICATIONS

This application is a continuation of, and claims the benefit of, my provisional application having Ser. No. 60/085,917, filed May 18, 1998, now abandoned.

BACKGROUND OF THE INVENTION (a) Field of the Invention

This invention generally relates to a supplement for organisms and to a method for enhancing the electrical currents through organic cells. More particularly, but not by way of limitation, to a supplement that includes water and dissolved energized or magnetized trace elements which are used to enhance the electrical environment within a cell by delivering the solution to the body by way of the bloodstream.

(b) Known Art

Biological diversity is an amazement of nature to which there is no equal. Within the recent past DNA (deoxyribonucleic acid) was discovered as the chemical component responsible for the biological diversity between all living entities. Unfortunately, to date the driving force behind DNA has been left unanswered by the mainstream biological community. Recent experiments have conclusively demonstrated that electricity flows through DNA. These electrical currents afforded to the DNA molecule explain how one molecule can control and direct the formation of a living organism. Viruses, bacteria, plants, animals, and man all owe their existence to two common entities DNA [RNA (ribonucleic acid) for some viruses] and electricity. Electricity is funneled through the individual codonal units giving each individual gene away to control its expression along a chemical trail to the expression of a physical entity.

SUMMARY

It has been discovered that electrical, or the closely related magnetic, fields play an important role in the way genes express or develop their innate maps for a physical entity. A way to supplement the electrical component of all living organisms has been discovered, and is disclosed herein. This is accomplished by passing electrical currents through elements and/or compounds in an aqueous environment. The elements and/or compounds gather electrical energy from the electrical current. The energized or magnetized elements are then given to the living organisms.

DETAILED DESCRIPTION OF EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Biological systems have long been known to direct and control electrical energy. The definition of death is the cessation of brain and heart electrical activity. Throughout the last century different forms of electrical supplementation have been used to supplement animals' pre-existing electrical fields. These previous attempts have met with different degrees of success. The supplementations have demonstrated window effects of both intensity and frequency. The windows have been found using the hit and miss approach. Robert Becker has consistently demonstrated enhanced healing of biological systems when the current densities are closest to those of the animals under study. Becker, Andrew Bassett and Andrew Marino have concentrated their efforts in the fields of regeneration and bone healing.

Commercial magnets are in the market place for humans, claiming enhanced well being. These are external magnets that are placed on different parts of the body to eliminate pain, increase well being and enhance sleep.

My system involves supplementing biological systems with electrified trace elements in an aqueous system. This involves the use of specific trace elements and/or compounds. The trace elements and/or compounds of choice would be those with magnetic, electromagnetic, paramagnetic, and diamagnetic properties. These elements, magnetized and/or energized, are placed in water where electrical currents are flowing. Once the elements are magnetized and/or energized they are ready for consumption. The elements are energized by passing direct current through the electrodes containing the elements. The anode slowly dissolves leaving the energized elements in solution. The magnetic elements may be placed in the solution that the electrical current is passing through, allowing them to become energized using metal and/or carbon electrodes. If carbon electrodes are used they do not dissolve into the aqueous environment, but charge the trace compounds in solution. Once these minerals are inside the body they would circulate through the blood stream. Any conducting element that is subjected to a changing magnetic field will have electrons induced into it, increasing electrical flow through that molecule. There are five advantages with this type of system. They are:

1. The magnetic field is in close proximity to the conducting elements of the body.

2. The magnetized minerals control their own frequency.

3. The proper levels of most minerals and vitamins have been established.

4. Most of the minerals and vitamins have gained approval by the FDA and USDA.

5. The low cost of the supplementation.

Metal electrodes placed in aqueous systems are capable of generating magnetic and electromagnetic compounds. The characteristics of the electrical currents have not yet been determined. Research will be conducted to see what voltages and amperages yield the best results.

Using twelve volts, direct current, passing through iron and niobium electrodes enabled piglets to be disease free when they were challenged by *Clostridium perfringes*. The energized metals were dissolved in the water supply of the sows. All of the control piglets (ninety litters) showed the typical bloody scours of *Clostridium perfringes* infection. All the treated piglets (thirty litters) were scour free. In the control piglets, mortality reached one hundred percent, unless the right antibiotic was used.

Electromagnetic supplementation will allow improved livability of any and all creatures given the supplementation. Looking at the whole body of man, Robert Becker mapped out "THE HUMAN DC FIELD PATTERN". The fields shows areas of negative and positive concentrations. The positive focal points of field polarity are the brain, and conjunction points with the arms and legs along the spinal cord. Other areas of the positive field were centered around acupuncture points throughout the body. The readings further indicated that electrical currents were flowing through the nervous system to the acupuncture points. Becker was under the false impression that electrons flow from positive to negative as Benjamin Franklin had theorized. In the past few years it has come to light that electrons flow from areas of negative polarity to the more positive area. Becker had electrons flowing in the wrong direction giving rise to false interpretations of what actually occurs in the body. Becker, R. O. & Bichell, D. (1985). *The Body Electric: Electromagnetism and the Foundation of Life*. New York: William Morrow and Company, Inc.

From Robert Becker we have further proof that DNA has control and direction throughout the body. The popular press uses the term "hard wired" when referring to the body. Cellular components of the body use these "wires" to direct electrical currents through enzymatic pathways electrochemically. Electrochemical control adds energy to the electrical system of the body. One volt defined electrically contains $3.83\times10^{-23}$ Kcal while one volt electrochemically contains 23.07 Kcal/mole. This raises the amount of energy contained in one volt by a factor of $6.023\times10^{23}$ which is the number of molecules in a mole, or Avagodro's number. The body deals with mass flow of electricity. Each and every cell of the body uses and controls the flow of electrons. Energy equals mass times velocity squared which is $E=mv^2$. Therefore when examining a living being the amount of energy being directed and controlled by DNA should be considered as a significant energy source. Taking an eighty kilogram man and adding 0.0025 volts to his body would add 256 Kcal of electrochemical energy to the body.

Niobium is a very unique element, ubiqouiste with an average concentration of 3 ppm. Niobium is superconducting and more magnetic than iron. Ferrous niobate has the magnetic capability equal to some of the best commercial magnets. Niobium has not been approved by any government agency for consumption. Natural sources of niobium are available. If health food stores are chosen as a source of distribution, then commercial production of niobium for consumption would be possible. Sand could serve as a source of niobium, using a magnet to extract all the magnetic material. The extracted magnetic material would then be pressed together to form the electrodes or use carbon electrodes and place the magnetic material in an aqueous solution. The material will be pre-sterilized before processing. The iron content of the magnetic material will be used to determine the supplementation level of the finished supplement. After passing the electrical current through the solution, the supplement would be ready for distribution.

Another option would be to use magnetite, which has been approved by the government for human consumption. Again the magnetite would be compressed to form the electrodes or use carbon electrodes and place the magnetite in the solution through which the current is passed. Metal electrodes may be used instead of or preferentially over carbon. Starting with the known trace metals, different combinations of metals should be tried to establish the best possible combination of electrodes and metals in solution. Bacterial screening should afford a speedy solution to figuring out the best combinations.

Recent experiments have conclusively demonstrated that DNA is a conductor of electrical energy. When we presently think of DNA, we see a molecule passively resting in the nucleus of a cell. DNA has no way of quickly communicating with rest of that cell let alone with other cells or the rest of the body. An active DNA can use electrical currents to direct and control cellular and bodily functions by specified electrical currents. Individual cells contain junctions, whose specific purpose is to control electrical current flow between cells. Having the body electrically connected would speed the spread of information throughout the body both for the gathering of information, and direction as determined by DNA. DNA should be able to control the electrical currents' voltage, amperage, and frequency through each three-pronged codon. Each mammalian gene contains approximately $5.5\times10^9$ codons. With several genes per DNA, finding the specified voltage and frequency for each codon would be a life's work.

The genome project presently being undertaken by the scientific community will greatly increase the likelihood that each of DNA's genes will be identified in the near future. If we could arouse the attention of the scientific community to add electrical currents to their search, then finding the proper frequency and intensity of ELFs (electromagnetic field) for biological supplementation could be accomplished. The literature of the past century has clearly demonstrated the biological effects of ELF's. The correlation of ELF's biological effects is most likely caused by DNA's control of electrical currents.

Another aspect of DNA's conductivity cannot be ignored. The more current flowing through the DNA the tighter the circle of its alpha helix. The tightening of the helix would decrease the vulnerability of DNA to invasive changes. The direction and control of DNA's information would be more forceful with electrical supplementation leading to a clearer flow of information. The tighter binding of the DNA would decrease the number of divisions per unit of time. The decrease in the number of cell divisions would increase life span by maintaining a higher number of telomeres per chromosome over any period of time.

If we look at the whole body, we can see that there are specific frequencies directed by DNA throughout the body. The heart rate is 1.07 Hz (64 beats per minute). The brain also has specified frequencies (alpha waves, beta waves, theta waves, delta waves, etc.). The liver is at 12 Hz, muscle is 4–12 Hz, stomach<1 Hz, etc. All of the individual organs operate at specific frequencies and each individual organ is electrically isolated by its' external membrane.

Another approach would be to use major organ frequencies: heart, brain, liver, kidney, etc. The organs' signals are directed by DNA. I have tried organ frequency supplementation and have found success using only single frequency pulsed magnetic fields for supplementation. A combination of several frequencies will achieve a complete response of biological systems to ELFs. The real problem with pulsed magnetic fields is that the fields fall off too quickly. The fields dissipate with the square of the distance; therefore, even a strong field dissipates over a short distance. Another application of pulsed magnetic fields would be to use the fields for repair, and to offset harmful genetic mutations. The return of proper functioning would greatly enhance the biological functioning of the individual. If the frequency of a normal gene is known, then the supplementation of the body with the proper frequency to alleviate the misdirection given by the mutated gene should, over time, revert the gene to its proper orientation. This would allow for normal functioning. Adding magnetic elements to the body should enhance the body's receptivity to ELFs.

With all of the body's frequencies directed by DNA, the question arises whether or not the electrical currents are sufficient to run the body at optimum levels. Bones are piezoelectric in nature. Upon deformation the bone generates electrical currents. Bones also have semiconductive properties with rectifiers to preferentially control the current's direction. The electron transport system of the mitochondria generates ATP (adenosine triphosphate) from ADP (adenosine diphosphate) along the electron transport chain for chemical energy used by the cells. The electron transport system is another place where electrons are generated. The electrons flow on iron based and copper based enzymes to oxygen. Artificially supplied magnetic compounds would increase the electron flow throughout this electron transport system. The nervous system also carries electrical currents. Ionic currents are passed along individual neurons to their synapses were chemical messengers are released to propagate the signal to the next neuron. Within the myelin sheath, direct currents flow with the electrical currents of healing. The nervous systems electrical components are semiconductive in nature along with rectification for current directional control. With this information, we now know of at least two systems that control and generate electrons. We can then assume that if the body has all the electricity that it needs, there would be no reason to generate and control electrons through specified systems.

Since the body has systems for the generation and control of electrons, there is the likelihood that electrical supplementation will lead to optimal performance of the body's electrical systems. Supplementation of the body's own electrical system can be carried out in several ways. One method is to use external magnetic fields whose frequency and intensities are tied to the internal workings of the body. If each codon operates at a specified frequency and intensity, this could be a long and arduous task to find all the optimal magnetic fields to supplement the body. We would also have to investigate when specific genes are in the on or off position to know whether or not to supplement their currents at any one time.

I believe that frequency and wattage determines the metals and/or vitamins that the body requires. These metals and vitamins would have optimal operating currents and frequencies, and these currents are what make certain trace elements required for specific enzymatic functions while others are toxic.

Animal studies are to be conducted to determine which supplement will be the most effective. I would like to start out with a conservative estimate of increased livability brought about by the electrical supplement. People have been informed that they only use ten to thirty percent of their brain. The ten to thirty percent use would hold true for other organs and systems of the body.

Ten to thirty percent increase in disease resistance could no doubt defeat quite a few micro-organisms. The illustration of disease resistance of swine confirms increased disease resistance to one lethal micro-organism, demonstrating disease fighting abilities equivalent to antibiotics!

The electrical supplementation needs to be taken daily for the full effects to be realized. The daily consumption will increase the amount of product consumed when compared to antibiotics which are taken on a need basis. Electrical supplementation works. The question remains how much of the body's total functioning may we gain through electrical supplementation. If we go conservative and say a ten percent increase in life expectancy is possible, then by most standards that is still of considerable benefit. To obtain the life span of Methuselah a combination of both the correct energized mineral supplementation and pulsed ELF's will have to be developed.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A solution for enhancing the electrical activity within a living organism having cells, the solution comprising:
   water; and
   a magnetized trace element in sufficient concentration to raise the electrochemical energy of the cells of the living organism.

2. A solution according to claim 1 wherein said trace elements is any element from the periodic table of elements.

3. A solution according to claim 1 wherein said magnetized trace element is niobate.

4. A solution according to claim 1 wherein said magnetized trace element is ferrous niobate.

5. A solution according to claim 1 wherein said magnetized trace element is magnetite.

6. A solution according to claim 1 wherein said trace element has been magnetized to affect the electric field associated with the DNA of a cell in the living organism.

7. An edible solution for enhancing the electromagnetic activity within a living organism having cells, the solution comprising:
   water; and
   a magnetized trace element dissolved in the water in sufficient concentration so as to raise the electrochemical energy of the cells of the living organism and so as to avoid toxicity to the living organism.

8. A solution according to claim 7 wherein said trace elements are selected from the group consisting essentially of: niobium, ferrous niobate, magnetite, and vitamins.

9. A solution according to claim 7 wherein said magnetized trace element is selected from the group of essential trace elements consisting essentially of: selenium, cobalt, copper, molybdenum, magnesium, zinc, iodine, manganese, chromium, potassium, bromine, nickel, tin, silica, vanadium, oxygen, carbon, nitrogen, calcium, and phosphorus.

10. A solution according to claim 7 wherein said magnetized trace element is ferrous niobate.

11. A solution according to claim 7 wherein said magnetized trace element is magnetite.

12. A solution according to claim 7 wherein said trace element has been magnetized to affect the electric field associated with the DNA of a cell in the living organism.

13. A solution according to claim 7 wherein said trace element has been delivered into solution by means of an electric current.

14. A method for enhancing the electromagnetic environment in a cell within a living organism having a circulatory system, the method comprising:
    providing a desired amount of water;
    dissolving a magnetizable trace element in the water to produce a solution of the trace element;
    magnetizing the dissolved trace element to a sufficient concentration to raise the electrochemical energy of the cells of the living organism; and
    delivering the solution of the trace element into the circulatory system of the living organism.

15. A method according to claim 14 wherein said step of dissolving is carried out by providing an anode containing the element to be dissolved and a cathode, and then immersing the anode and cathode in the water and then delivering an electric current between the anode and cathode.

16. A method according to claim 15 wherein said step of delivering the solution of the trace element into the circulatory system of the living organism is carried out by feeding the solution to the living organism.

17. A method according to claim 14 wherein said trace elements are selected from the group consisting essentially of: niobium, ferrous niobate, and magnetite.

18. A solution according to claim 14 wherein said trace element is further magnetized by providing an electric field thought the solution.

19. A solution according to claim 14 wherein said magnetized trace element is ferrous niobate.

20. A solution according to claim 14 wherein said trace element has been magnetized to affect the electric field associated with the DNA of a cell in the living organism.

* * * * *